(12) United States Patent
Tanaka et al.

(10) Patent No.: US 11,534,377 B2
(45) Date of Patent: *Dec. 27, 2022

(54) HAIR GROWTH AGENT

(71) Applicant: KOBAYASHI PHARMACEUTICAL CO., LTD., Osaka (JP)

(72) Inventors: Kosuke Tanaka, Osaka (JP); Mihoko Kawasaki, Osaka (JP); Hironori Tomi, Osaka (JP); Takashi Tsuji, Tokyo (JP)

(73) Assignee: KOBAYASHI PHARMACEUTICAL CO., LTD., Osaka (JP)

( * ) Notice: Subject to any disclaimer, the term of this patent is extended or adjusted under 35 U.S.C. 154(b) by 86 days.

This patent is subject to a terminal disclaimer.

(21) Appl. No.: 17/158,838

(22) Filed: Jan. 26, 2021

(65) Prior Publication Data
US 2021/0145713 A1    May 20, 2021

Related U.S. Application Data

(63) Continuation of application No. 16/096,210, filed as application No. PCT/JP2017/016783 on Apr. 27, 2017, now Pat. No. 10,933,001.

(30) Foreign Application Priority Data

Apr. 27, 2016  (JP) ................... 2016-100903
Apr. 28, 2016  (JP) ................... 2016-091063

(51) Int. Cl.
| | | |
|---|---|---|
| A61K 8/34 | (2006.01) | |
| A61Q 7/00 | (2006.01) | |
| A61K 31/047 | (2006.01) | |

(52) U.S. Cl.
CPC .............. A61K 8/34 (2013.01); A61K 31/047 (2013.01); A61Q 7/00 (2013.01)

(58) Field of Classification Search
CPC ......... A61P 17/14; A61K 31/047; A61K 8/34; A61Q 7/00
See application file for complete search history.

(56) References Cited

U.S. PATENT DOCUMENTS

| | | | |
|---|---|---|---|
| 5,043,162 A * | 8/1991 | Trager .................. | A61K 8/345 514/400 |
| 5,091,596 A | 2/1992 | Kennington et al. | |
| 5,124,360 A | 6/1992 | Larner et al. | |
| 5,428,066 A | 6/1995 | Larner et al. | |
| 5,906,979 A | 5/1999 | Allan | |
| 2002/0032177 A1 | 3/2002 | Allan et al. | |
| 2002/0143039 A1 | 10/2002 | Krajcik et al. | |
| 2008/0138379 A1 | 6/2008 | Jennings-Spring | |

FOREIGN PATENT DOCUMENTS

| | | |
|---|---|---|
| EP | 2116224 A1 | 11/2009 |
| JP | 2-45407 A | 2/1990 |
| JP | 2006-28026 A | 2/2006 |
| WO | WO 01/62237 A2 | 8/2001 |

OTHER PUBLICATIONS

"Disease state of insulin resistance and administration thereof—Usability and limitation of HbA1C as inspection index", Information box & net of diabetes for medical staff—No. 13, Jul. 2007, with partial English translation.
"Inositol", printed Sep. 9, 2020, https://www.sigmaaldrich.com/catalog/product/usp/1340960?lang=en&region=US.
"Inositol", Wikipedia, printed Sep. 9, 2020, https://en.wikipedia.org/wiki/inositol.
"Inositols", printed Aug. 28, 2020, https://www.tcichemicals.com/JP/ja/support-download/tcimail/application/125-13 with partial English translation.
"Japanese Pharmaceutical Excipients 2003," Yakuji Nippo, Limited, pp. 101-102 (6 pages total), with English translation.
"Metabolic syndrome and disease model", Funakoshi review No. 1, http://www.funakoshi.co.jp/contents/94: published on Mar. 31, 2008, with partial English translation.
"Metoformin hydrochloride salt, Application for approval of manufacturing and distribution, CTD part 2, 2.4 Global assessment regarding non-clinic", Jan. 20, 2010, Sumitomo Dainippon Pharma Co., Ltd. with partial English translation.
"Japanese Pharmaceutical Excipients Directory 2000," Yakuji Nippo, Limited, 2000, pp. 26 (3 pages total), with English translation.
"The Japanese Standards of Quasi-drug Ingredients 2006 Consolidated Edition," Yakuji Nippo, Limited, 2006, pp. 318 (5 pages total), with English translation.
English translation of the International Search Report (form PCT/ISA/210), dated Jul. 25, 2017, for International Application No. PCT/JP2017/016783.
Extended European Search Report for European Application No. 17789674.3, dated Dec. 12, 2019.
Joslin's Diabetes Mellitus 2nd edition, published Mar. 1, 2007, p. 553, with partial English translation.
Mark P. Thomas, et al.,"The "Other" Inositols and Their Phosphates: Synthesis, Biology and Medicine (with Recent Advances in myo-Inositol Chemistry)", Angewandte Chemie International, vol. 55, No. 5, Dec. 22, 2015.
Pierard et al., "The skin landscape in diabetes mellitus. Focus on dermocosmetic management", Clinical, Cosmetic and Investigational Dermatology, May 14, 2013, vol. 6, pp. 127-135.
Shum, Kid Wan et al., "Hair loss in women with hyperandrogenism: Four cases responding to finasteride", J. Am Acad Dermatol., vol. 47, No. 5, Nov. 2002, pp. 733-739.

(Continued)

Primary Examiner — Umamaheswari Ramachandran
(74) Attorney, Agent, or Firm — Birch, Stewart, Kolasch & Birch, LLP

(57) ABSTRACT

The present invention is directed to a hair growth agent for external use comprising chiro-inositol, which is provided as an excellent hair growth agent.

10 Claims, 10 Drawing Sheets

(56) References Cited

OTHER PUBLICATIONS

Taru Garg et al., "Drug-induced diffuse hair loss in females: An observational study", Astrocyte, vol. 1, Issue 2, pp. 80-83, 2014.
Toshiro Kubota, "Update in polycystic ovary syndrome: new criteria of diagnosis and treatment in Japan", Reprod Med Biol, vol. 12, No. 3, pp. 71-77, Jul. 2013.

* cited by examiner

NEGATIVE CONTROL: PBS
TEST SOLUTION A1: 0.05 wt% D-chiro-INOSITOL
TEST SOLUTION A2: 0.1 wt% D-chiro-INOSITOL
TEST SOLUTION A3: 1 wt% D-chiro-INOSITOL
TEST SOLUTION B1: 0.05 wt% myo-INOSITOL
TEST SOLUTION B2: 0.1 wt% myo-INOSITOL
TEST SOLUTION B3: 1 wt% myo-INOSITOL

HAIR GROWTH AGENT

CROSS REFERENCE TO RELATED APPLICATIONS

This application is a Continuation of copending application Ser. No. 16/096,210, filed on Oct. 24, 2018, which was filed as PCT International Application No. PCT/JP2017/016783 on Apr. 27, 2017, which claims the benefit under 35 U.S.C. § 119(a) to Patent Application No. 2016-091063, filed in Japan on Apr. 28, 2016, and Patent Application No. 2016-100903, filed in Japan on Apr. 27, 2016, all of which are hereby expressly incorporated by reference into the present application.

TECHNICAL FIELD

The present invention relates to a hair growth agent and more specifically relates to a hair growth agent for external use comprising chiro-inositol.

BACKGROUND ART

As a reflection of the aging and stressful society, demand for hair growth agents has been growing. Hair typically repeats a cycle (hair cycle) of elongation from the hair papilla that accompanies hair matrix cell division and of shedding in which hair is pushed upward following termination of hair matrix cell division, thereby separating the hair root from the hair papilla. The hair cycle consists of the anagen phase in which a hair root and a hair shaft elongate; the catagen phase in which hair matrix cell division is arrested and the elongation gradually decreases while the connection between the hair root and the hair papilla loosens; and the telogen phase in which hair sheds and the hair papilla rests. In a period from the telogen phase to the anagen phase of the hair cycle, a new hair follicle is formed.

Inositol (1,2,3,4,5,6-cyclohexanehexaol) is a compound known as a vitamin-like substance having a structure in which one hydrogen atom on each carbon of cyclohexane is substituted with a hydroxyl group. Inositol exists as 9 stereoisomers corresponding to combinations of steric configurations of hydroxyl groups. As an excipient for pharmaceuticals and quasi-drugs, myo-inositol (cis-1,2,3,5-trans-4,6-cyclohexanehexaol) is used under the name of inositol (inosit) (Non-Patent Literature (NPL) 1 to 3). A hair growth agent containing inositol as a component has been reported (Patent Literature (PTL) 1). Further, it has been reported that insulin sensitivity increasing substances (ISIS) were effective for treatment of hair loss associated with insulin resistance and that metformin and troglitazone, as specific examples of ISIS, prevented hair loss or slowed progress of hair loss in obese mice (PTL 2).

CITATION LIST

Patent Literature

PTL 1: JP 2006-28026
PTL 2: WO 2001/062237

Non-Patent Literature

NPL 1: The Japanese Standards of Quasi-Drug Ingredients 2006 consolidated edition, Yakuji Nippo, Limited, p. 318
NPL 2: Japanese Pharmaceutical Excipients 2003, Yakuji Nippo, Limited, pp. 101-102
NPL 3: Japanese Pharmaceutical Excipients Directory 2000, Yakuji Nippo, Limited, p. 26

SUMMARY OF INVENTION

Technical Problem

An object of the present invention is to provide a hair growth agent having excellent hair growth effects.

Solution to Problem

As a result of continued intensive research to achieve the above object, the present inventors found that only chiro-inositol, among the stereoisomers of inositol, has excellent hair growth activity, thereby achieving the present invention.

The present invention provides the following inventions.

[1] A hair growth agent for external use comprising chiro-inositol.

[2] The hair growth agent according to [1], wherein chiro-inositol is the D isomer.

[3] The hair growth agent according to [1] or [2], wherein chiro-inositol content is 0.001 to 20 wt % based on a total weight.

[4] The hair growth agent according to any one of [1] to [3], wherein chiro-inositol content is 0.01 to 10 wt % based on the total weight.

[5] The hair growth agent according to any one of [1] to [4], wherein the hair growth agent is used for promoting hair shaft growth or for growing new hair.

[6] The hair growth agent according to any one of [1] to [5], wherein the hair growth agent is used for increasing an elongation rate of a hair shaft.

[7] The hair growth agent according to any one of [1] to [5], wherein the hair growth agent is used for increasing a maximum length of a hair shaft.

[8] The hair growth agent according to any one of [1] to [5], wherein the hair growth agent is used for increasing a hair shaft diameter.

[9] The hair growth agent according to any one of [1] to [5], wherein the hair growth agent is used for increasing a hair count.

[10] The hair growth agent according to any one of [1] to [5] and [9], wherein the hair growth agent is used for promoting new hair growth from a pore where new hair growth has been arrested or ability of the pores to grow new hair has decreased.

[11] The hair growth agent according to any one of [1] to [5], [9], and [10], wherein the hair growth agent is used for shortening the telogen phase in a hair cycle.

[12] The hair growth agent according to any one of [1] to [5], [9], and [10], wherein the hair growth agent is used for resuming an arrested hair cycle.

[13] The hair growth agent according to any one of [1] to [12], wherein the hair growth agent is a solution.

[14] The hair growth agent according to any one of [1] to [13], wherein the hair growth agent is used for human scalp hair.

[15] A method of growing hair comprising administering the hair growth agent according to any one of [1] to [14] to a subject.

Advantageous Effects of Invention

According to the present invention, an excellent hair growth agent is provided.

DESCRIPTION OF EMBODIMENTS

Figure 1:
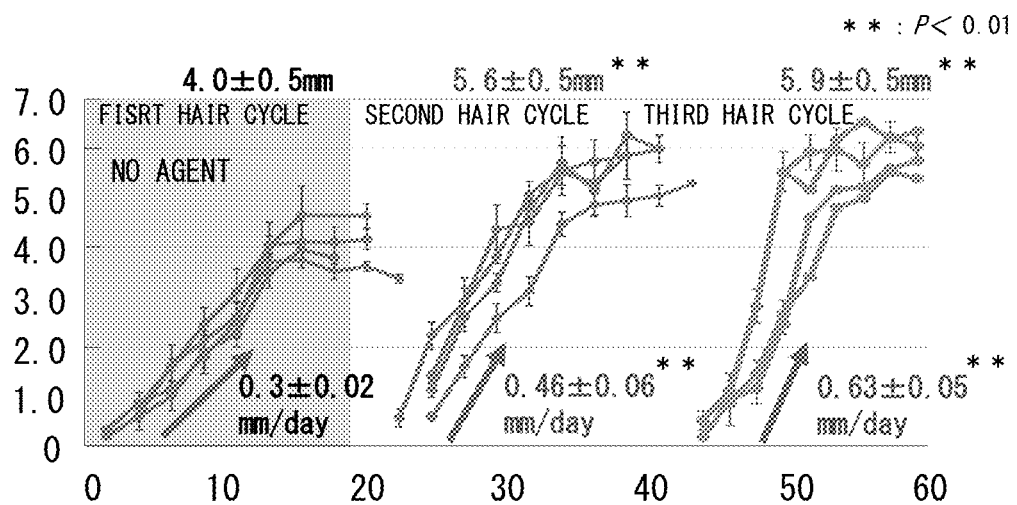
FIG. 1 is a chart showing changes in hair shaft length in sites of mice where a 50% ethanol aqueous solution containing D-chiro-inositol (10 wt %) was applied. The vertical axis represents hair shaft length (mm) and the horizontal axis represents the number of days. Here, the first hair cycle shows reference data in which a 50% ethanol aqueous solution not containing the agent was applied.

Hereinafter, a hair growth agent of the present invention will be described.

A hair growth agent of the present invention is a hair growth agent for external use comprising chiro-inositol.

In the present invention, chiro-inositol may be extracted from buckwheat, pulses, and citrus fruits, for example, where it naturally exists; may be extracted from that produced through fermentation of legumes and the like; or may be chemically synthesized. Further, chiro-inositol is also available for purchase.

The content of chiro-inositol in a hair growth agent of the present invention is, for example, 0.001 to 20 wt %, specifically 0.01 to 10 wt %, and more specifically 0.1 to 10 wt % based on the total weight of the hair growth agent.

Further specifically, the content of chiro-inositol in the hair growth agent of the present invention is 0.3 to 5 wt %, still further specifically 0.5 to 3 wt %, and most specifically 0.7 to 1 wt % based on the total weight of the hair growth agent.

A hair growth agent of the present invention is applicable to external pharmaceuticals, pseudo-drugs, cosmetics (including hair cosmetics and scalp cosmetics), and the like. For example, the hair growth agent may be used as ointment, poultices, liniment, lotion, liquids for external use, dusting powder, cream, gel, milky lotion, hair tonics, and hair sprays, but is not limited to these uses.

A hair growth agent of the present invention may contain other components, such as commonly acceptable excipients for pharmaceuticals, pseudo-drugs, and cosmetics (including hair cosmetics and scalp cosmetics), in addition to chiro-inositol as an active ingredient. Examples of other components, such as excipients, include vehicles, stabilizers, flavoring agents, bases, dispersants, diluents, surfactants, emulsifiers, transdermal absorption promoting agents, pH adjusting agents, preservatives, colorants, oil (fats and oils, mineral oil, and the like), humectants, alcohols, thickeners, polymers, film forming agents, UV absorbers, cell activators, antioxidants, antiseptics, fresheners, deodorants, pigments, dyes, perfume, sugars, amino acids, vitamins, organic acids, organic amines, and plant extracts, but are not limited to these components.

A hair growth agent of the present invention may contain commonly known components that are effective, for example, for growing (new) hair and for nourishing hair.

The amount of chiro-inositol administered per dose of a hair growth agent of the present invention is, for example, 0.005 to 200 mg, specifically 0.05 to 100 mg, and more specifically 0.5 to 10 mg.

The administration frequency of a hair growth agent of the present invention is, for example, 1 to 6 times per day, specifically 1 to 3 times per day, and more specifically once or twice per day.

A hair growth agent of the present invention concerns promotion of hair shaft growth, new hair growth, and hair loss prevention, and preferably concerns promotion of hair shaft growth and new hair growth.

The phrase "promotion of hair shaft growth" herein means an increased elongation rate, an increased maximum length, and/or an increased diameter of a hair shaft.

The term "new hair growth" herein means an increased hair count through promotion of new hair growth from pores where new hair growth has been arrested or ability of the pores to grow new hair has decreased in sites without hair (no hair shaft protruding from the epidermis) or with a low hair count. Specifically, the term means shortening of the telogen phase in a hair cycle and/or resuming of an arrested hair cycle.

The phrase "effect on promotion of hair shaft growth" herein means an advantageous effect exerted on promotion of hair shaft growth, and characteristics exhibiting the effect on promotion of hair shaft growth are referred to as "hair shaft growth promoting activity". Further, the phrase "effect on new hair growth" means an advantageous effect exerted on new hair growth, and characteristics exhibiting the effect on new hair growth are referred to as "new hair growth promoting activity".

The term "hair loss" herein refers to a shedding phenomenon of hair shafts from pores and specifically indicates increased inhibitory cytokines and the like that inhibit cell proliferation, as well as cell death thereof. Characteristics exhibiting an effect on prevention of hair loss are referred to as "hair loss preventive activity". Further, the "effect on prevention of hair loss" means a decreased shedding count of hair shafts from pores by inhibiting or decreasing inhibitory cytokines and suppressing cell death, and represents a physiological phenomenon different from the characteristics exhibiting the effect on promotion of hair shaft growth or new hair growth. A hair growth agent of the present invention effectively prevents hair loss also in non-insulin-resistant users.

A hair growth agent of the present invention may be used for increasing an elongation rate of a hair shaft or increasing a maximum length of a hair shaft. An elongation rate of a hair shaft can be increased, for example, by maximum of about 110%, specifically by about 25 to 110%, and more specifically by about 33 to 110% compared with an elongation rate of a hair shaft in reference data of a hair cycle. A maximum length of a hair shaft can be increased, for example, by maximum of about 49%, specifically by about 1 to 49%, and more specifically by about 2 to 49%.

A hair growth agent of the present invention may be used for increasing a hair shaft diameter.

A hair growth agent of the present invention may be used for increasing a hair count through promotion of new hair growth from pores where new hair growth has been arrested or ability of the pores to grow new hair has decreased in sites without hair (no hair shaft protruding from the epidermis) or with a low hair count. Specifically, the hair growth agent may be used for shortening the telogen phase in a hair cycle and/or resuming an arrested hair cycle.

In one embodiment, a hair growth agent of the present invention does not include an application, for example, to hair loss associated with insulin resistance.

A hair growth agent of the present invention is also applicable to animals, such as livestock and pets, in addition to humans. In one aspect of the present invention, a hair growth method (excluding medical practice) comprising administering an agent for external use comprising chiro-inositol to a subject is provided.

EXAMPLES

Example 1 Evaluation of D-chiro-Inositol Hair Growth Activity (1)

Hair follicles (surgically prepared) of haired mice were transplanted into the back of nude mice (from Sankyo Labo Service Corporation, Inc.) to produce transplanted mice manipulated such that each hair can be distinguished and a plurality of hair cycles can be observed.

First, a 50% ethanol aqueous solution (12.5 μl, not containing the agent) was applied to the transplanted mice 4 times per day during new hair growth in the first hair cycle to obtain reference data of a hair cycle. After the hair had shed following the end of the first hair cycle, a 50% ethanol aqueous solution (12.5 μl) containing a predetermined amount of the agent was applied to the mice 4 times per day to obtain data on effects of the agent. After the hair had shed following the end of the second hair cycle, a 50% ethanol aqueous solution (12.5 μl) containing the agent in the same amount as that in the second hair cycle was applied to the mice in a similar manner to the second hair cycle to obtain reproducibility data on effects of the agent.

As the agent, D-chiro-inositol (from Wako Pure Chemical Industries Ltd.) and its stereoisomers as chiro-inositol, L-chiro-inositol (from Tokyo Chemical Industry Co., Ltd.), myo-inositol (from Wako Pure Chemical Industries Ltd.), allo-inositol (cis-1,2,3,4-trans-5,6-cyclohexanehexaol) (from Tokyo Chemical Industry Co., Ltd.), epi-inositol (cis-1,2,3,4,5-trans-6-cyclohexanehexaol) (from Tokyo Chemical Industry Co., Ltd.), muco-inositol (cis-1,2,4,5-trans-3,6-cyclohexanehexaol) (from Tokyo Chemical Industry Co., Ltd.), and scyllo-inositol (cis-1,3,5-trans-2,4,6-cyclohexanehexaol) (from Tokyo Chemical Industry Co., Ltd.) were used.

For each agent solution, the lengths of hair shafts were measured every 2 to 3 days, an average length of hair shafts that changed day by day was plotted as one dot at each time point in a graph, and a similar plotting was repeated for 3 to 4 mice. The results were shown in Tables 1 to 14 and FIGS. 1 to 14.

TABLE 1

Results of D-chiro-inositol (10 wt %)

|  | Reference data (first hair cycle) | Data on effects of the agent (second hair cycle) | Reproducibility data on effects of the agent (third hair cycle) |
| --- | --- | --- | --- |
| Hair shaft growth rate (mm/day) | 0.30 ± 0.02 | 0.46 ± 0.06** | 0.63 ± 0.05** |
| Relative to reference data | — | 154% | 210% |
| Hair shaft maximum length (mm) | 4.0 ± 0.5 | 5.6 ± 0.5** | 5.9 ± 0.5** |
| Relative to reference data | — | 142% | 149% |

TABLE 2

Results of D-chiro-inositol (5 wt %)

|  | Reference data (first hair cycle) | Data on effects of the agent (second hair cycle) | Reproducibility data on effects of the agent (third hair cycle) |
| --- | --- | --- | --- |
| Hair shaft growth rate (mm/day) | 0.36 ± 0.05 | 0.46 ± 0.04* | 0.49 ± 0.07* |
| Relative to reference data | — | 128% | 136% |
| Hair shaft maximum length (mm) | 4.4 ± 0.3 | 5.1 ± 0.3** | 5.1 ± 0.4** |
| Relative to reference data | — | 116% | 116% |

TABLE 3

Results of D-chiro-inositol (1 wt %)

|  | Reference data (first hair cycle) | Data on effects of the agent (second hair cycle) | Reproducibility data on effects of the agent (third hair cycle) |
| --- | --- | --- | --- |
| Hair shaft growth rate (mm/day) | 0.39 ± 0.01 | 0.47 ± 0.01** | 0.48 ± 0.04* |
| Relative to reference data | — | 121% | 123% |
| Hair shaft maximum length (mm) | 5.1 ± 0.4 | 5.7 ± 0.4** | 6.0 ± 0.4** |
| Relative to reference data | — | 110% | 116% |

TABLE 4

Results of D-chiro-inositol (0.1 wt %)

|  | Reference data (first hair cycle) | Data on effects of the agent (second hair cycle) | Reproducibility data on effects of the agent (third hair cycle) |
| --- | --- | --- | --- |
| Hair shaft growth rate (mm/day) | 0.30 ± 0.03 | 0.30 ± 0.03 | 0.40 ± 0.06 |
| Hair shaft maximum length (mm) | 4.6 ± 0.5 | 4.7 ± 0.4 | 4.8 ± 0.4** |
| Relative to reference data | — | 101% | 105% |

TABLE 5

| Results of D-chiro-inositol (0.01 wt %) | | | |
|---|---|---|---|
| | Reference data (first hair cycle) | Data on effects of the agent (second hair cycle) | Reproducibility data on effects of the agent (third hair cycle) |
| Hair shaft growth rate (mm/day) | 0.30 ± 0.03 | 0.30 ± 0.03 | 0.40 ± 0.06 |
| Hair shaft maximum length (mm) | 4.6 ± 0.3 | 4.8 ± 0.4 | 4.7 ± 0.3 |

TABLE 6

| Results of L-chiro-inositol (5 wt %) | | | |
|---|---|---|---|
| | Reference data (first hair cycle) | Data on effects of the agent (second hair cycle) | Reproducibility data on effects of the agent (third hair cycle) |
| Hair shaft growth rate (mm/day) | 0.35 ± 0.07 | 0.33 ± 0.08 | 0.33 ± 0.13 |
| Hair shaft maximum length (mm) | 5.1 ± 0.3 | 4.9 ± 0.7 | 4.8 ± 0.8 |

TABLE 7

| Results of myo-inositol (5 wt %) | | | |
|---|---|---|---|
| | Reference data (first hair cycle) | Data on effects of the agent (second hair cycle) | Reproducibility data on effects of the agent (third hair cycle) |
| Hair shaft growth rate (mm/day) | 0.37 ± 0.02 | 0.37 ± 0.05 | 0.39 ± 0.06 |
| Hair shaft maximum length (mm) | 4.6 ± 0.4 | 4.6 ± 0.5 | 4.7 ± 0.5 |

TABLE 8

| Results of myo-inositol (1 wt %) | | | |
|---|---|---|---|
| | Reference data (first hair cycle) | Data on effects of the agent (second hair cycle) | Reproducibility data on effects of the agent (third hair cycle) |
| Hair shaft growth rate (mm/day) | 0.40 ± 0.09 | 0.45 ± 0.03 | 0.44 ± 0.08 |
| Hair shaft maximum length (mm) | 4.9 ± 0.5 | 4.9 ± 0.5 | 5.0 ± 0.5 |

TABLE 9

| Results of allo-inositol (5 wt %) | | | |
|---|---|---|---|
| | Reference data (first hair cycle) | Data on effects of the agent (second hair cycle) | Reproducibility data on effects of the agent (third hair cycle) |
| Hair shaft growth rate (mm/day) | 0.43 ± 0.05 | 0.43 ± 0.02 | 0.40 ± 0.03 |
| Hair shaft maximum length (mm) | 5.6 ± 0.3 | 5.5 ± 0.3 | 5.5 ± 0.8 |

TABLE 10

| Results of allo-inositol (1 wt %) | | | |
|---|---|---|---|
| | Reference data (first hair cycle) | Data on effects of the agent (second hair cycle) | Reproducibility data on effects of the agent (third hair cycle) |
| Hair shaft growth rate (mm/day) | 0.40 ± 0.02 | 0.37 ± 0.03 | 0.40 ± 0.04 |
| Hair shaft maximum length (mm) | 5.1 ± 0.4 | 5.0 ± 0.5 | 5.2 ± 0.5 |

TABLE 11

| Results of epi-inositol (5 wt %) | | | |
|---|---|---|---|
| | Reference data (first hair cycle) | Data on effects of the agent (second hair cycle) | Reproducibility data on effects of the agent (third hair cycle) |
| Hair shaft growth rate (mm/day) | 0.32 ± 0.06 | 0.33 ± 0.09 | 0.32 ± 0.09 |
| Hair shaft maximum length (mm) | 4.7 ± 0.7 | 4.7 ± 0.6 | 4.5 ± 0.6 |

TABLE 12

| Results of epi-inositol (1 wt %) | | | |
|---|---|---|---|
| | Reference data (first hair cycle) | Data on effects of the agent (second hair cycle) | Reproducibility data on effects of the agent (third hair cycle) |
| Hair shaft growth rate (mm/day) | 0.45 ± 0.03 | 0.43 ± 0.06 | 0.45 ± 0.09 |
| Hair shaft maximum length (mm) | 5.2 ± 0.3 | 5.2 ± 0.3 | 5.3 ± 0.4 |

TABLE 13

Results of muco-inositol (5 wt %)

|  | Reference data (first hair cycle) | Data on effects of the agent (second hair cycle) | Reproducibility data on effects of the agent (third hair cycle) |
|---|---|---|---|
| Hair shaft growth rate (mm/day) | 0.33 ± 0.07 | 0.35 ± 0.03 | 0.36 ± 0.10 |
| Hair shaft maximum length (mm) | 5.0 ± 0.3 | 4.9 ± 0.3 | 5.1 ± 0.3 |

TABLE 14

Results of scyllo-inositol (5 wt %)

|  | Reference data (first hair cycle) | Data on effects of the agent (second hair cycle) | Reproducibility data on effects of the agent (third hair cycle) |
|---|---|---|---|
| Hair shaft growth rate (mm/day) | 0.36 ± 0.07 | 0.35 ± 0.09 | 0.35 ± 0.09 |
| Hair shaft maximum length (mm) | 4.4 ± 0.5 | 4.4 ± 0.3 | 4.4 ± 0.5 |

In Tables 1 to 14, the mark * indicates significance with $p<0.05$, and the mark ** indicates significance with $p<0.01$.

Figure 2:
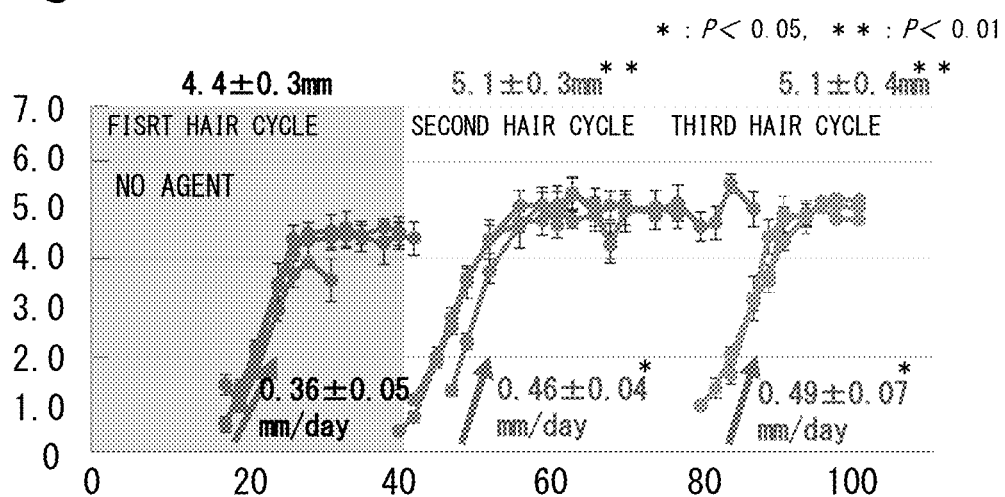
FIG. 2 is a chart showing changes in hair shaft length in sites of mice where a 50% ethanol aqueous solution containing D-chiro-inositol (5 wt %) was applied. The vertical axis represents hair shaft length (mm) and the horizontal axis represents the number of days. Here, the first hair cycle shows reference data in which a 50% ethanol aqueous solution not containing the agent was applied.
Figure 3:
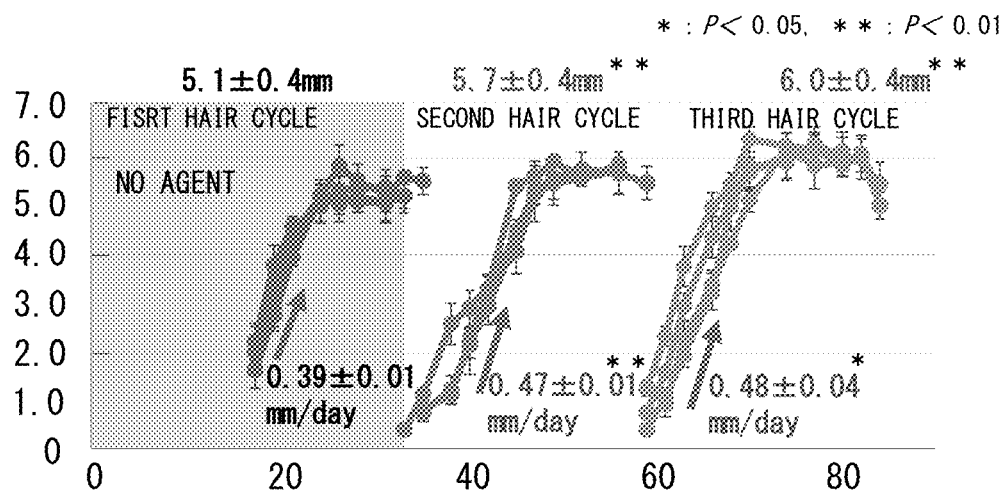
FIG. 3 is a chart showing changes in hair shaft length in sites of mice where a 50% ethanol aqueous solution containing D-chiro-inositol (1 wt %) was applied. The vertical axis represents hair shaft length (mm) and the horizontal axis represents the number of days. Here, the first hair cycle shows reference data in which a 50% ethanol aqueous solution not containing the agent was applied.
Figure 4:
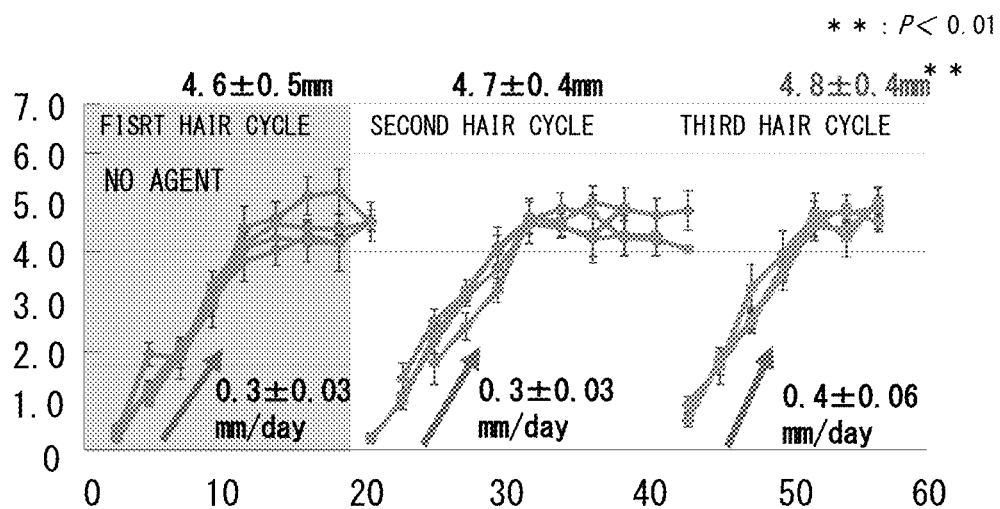
FIG. 4 is a chart showing changes in hair shaft length in sites of mice where a 50% ethanol aqueous solution containing D-chiro-inositol (0.1 wt %) was applied. The vertical axis represents hair shaft length (mm) and the horizontal axis represents the number of days. Here, the first hair cycle shows reference data in which a 50% ethanol aqueous solution not containing the agent was applied.
Figure 5:
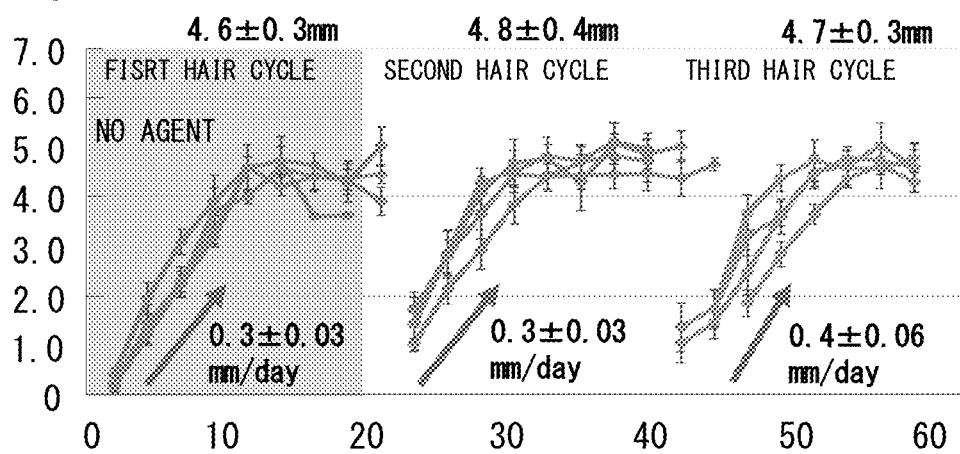
FIG. 5 is a chart showing changes in hair shaft length in sites of mice where a 50% ethanol aqueous solution containing D-chiro-inositol (0.01 wt %) was applied. The vertical axis represents hair shaft length (mm) and the horizontal axis represents the number of days. Here, the first hair cycle shows reference data in which a 50% ethanol aqueous solution not containing the agent was applied.
Figure 6:
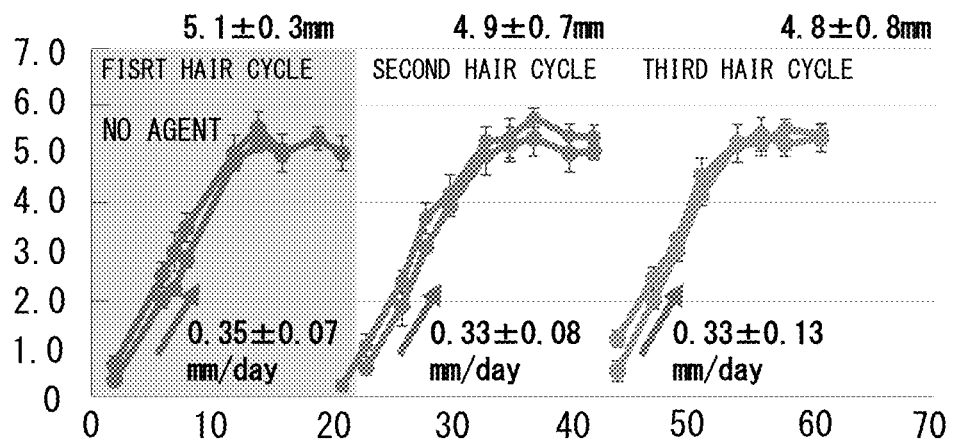
FIG. 6 is a chart showing changes in hair shaft length in sites of mice where a 50% ethanol aqueous solution containing L-chiro-inositol (5 wt %) was applied. The vertical axis represents hair shaft length (mm) and the horizontal axis represents the number of days. Here, the first hair cycle shows reference data in which a 50% ethanol aqueous solution not containing the agent was applied.
Figure 7:
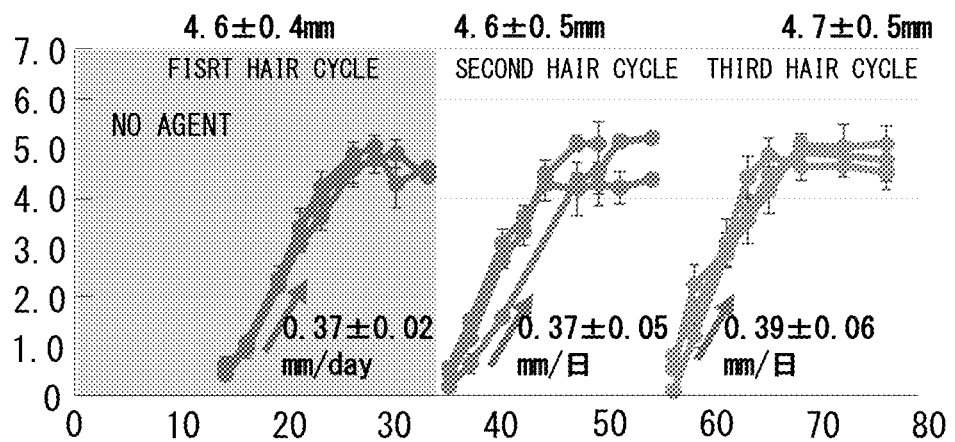
FIG. 7 is a chart showing changes in hair shaft length in sites mice where a 50% ethanol aqueous solution containing myo-inositol (5 wt %) was applied. The vertical axis represents hair shaft length (mm) and the horizontal axis represents the number of days. Here, the first hair cycle shows reference data in which a 50% ethanol aqueous solution not containing the agent was applied.
Figure 8:
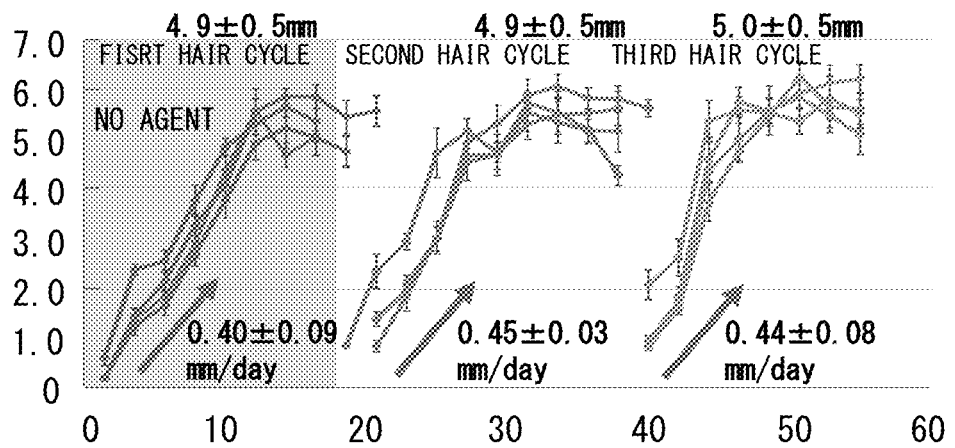
FIG. 8 is a chart showing changes in hair shaft length in sites of mice where a 50% ethanol aqueous solution containing myo-inositol (1 wt %) was applied. The vertical axis represents hair shaft length (mm) and the horizontal axis represents the number of days. Here, the first hair cycle shows reference data in which a 50% ethanol aqueous solution not containing the agent was applied.
Figure 9:
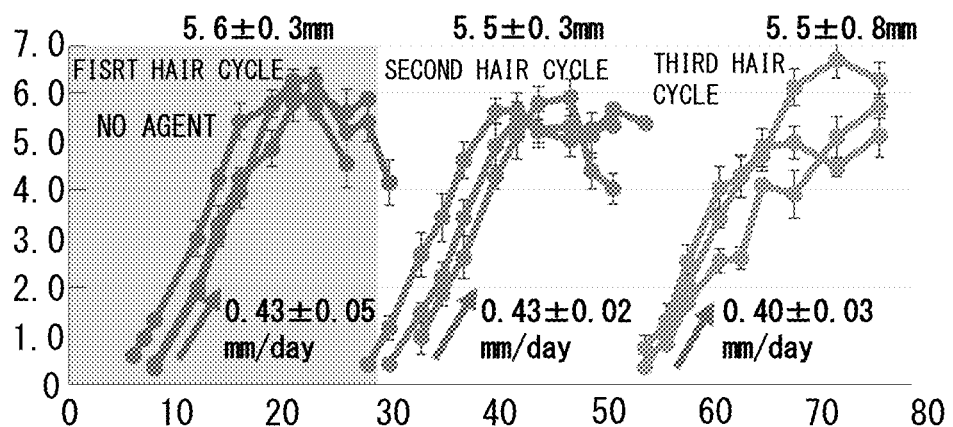
FIG. 9 is a chart showing changes in hair shaft length in sites of mice where a 50% ethanol aqueous solution containing allo-inositol (5 wt %) was applied. The vertical axis represents hair shaft length (mm) and the horizontal axis represents the number of days. Here, the first hair cycle shows reference data in which a 50% ethanol aqueous solution not containing the agent was applied.
Figure 10:
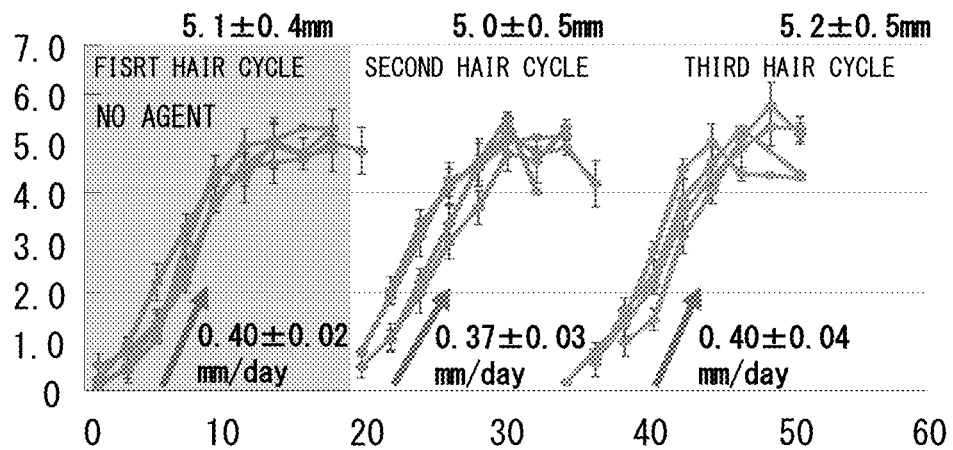
FIG. 10 is a chart showing changes in hair shaft length in sites of mice where a 50% ethanol aqueous solution containing allo-inositol (1 wt %) was applied. The vertical axis represents hair shaft length (mm) and the horizontal axis represents the number of days. Here, the first hair cycle shows reference data in which a 50% ethanol aqueous solution not containing the agent was applied.
Figure 11:
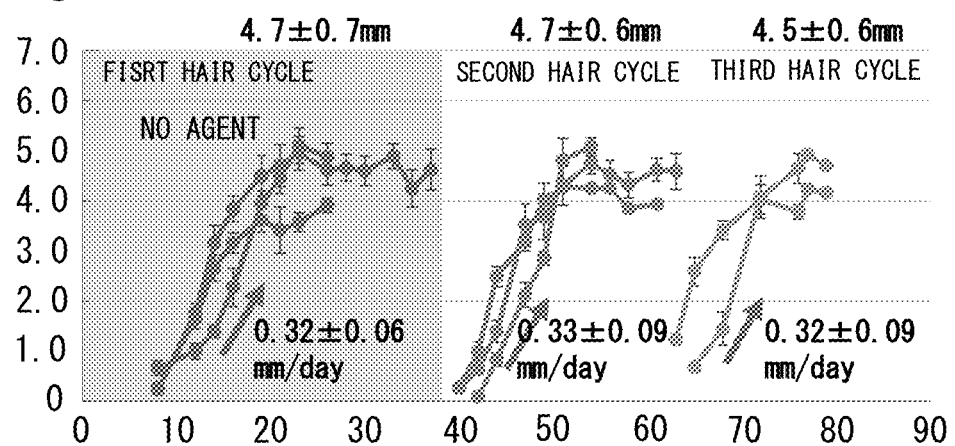
FIG. 11 is a chart showing changes in hair shaft length in sites of mice where a 50% ethanol aqueous solution containing epi-inositol (5 wt %) was applied. The vertical axis represents hair shaft length (mm) and the horizontal axis represents the number of days. Here, the first hair cycle shows reference data in which a 50% ethanol aqueous solution not containing the agent was applied.
Figure 12:
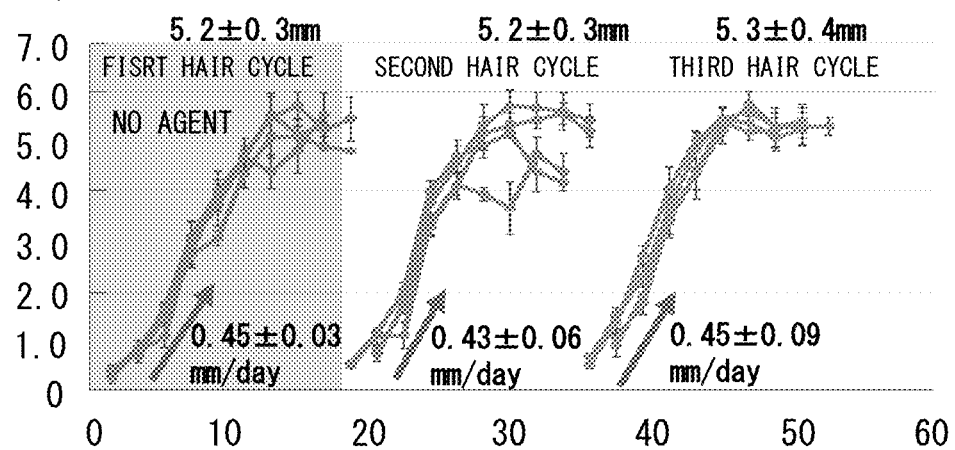
FIG. 12 is a chart showing changes in hair shaft length in sites of mice where a 50% ethanol aqueous solution containing epi-inositol (1 wt %) was applied. The vertical axis represents hair shaft length (mm) and the horizontal axis represents the number of days. Here, the first hair cycle shows reference data in which a 50% ethanol aqueous solution not containing the agent was applied.
Figure 13:
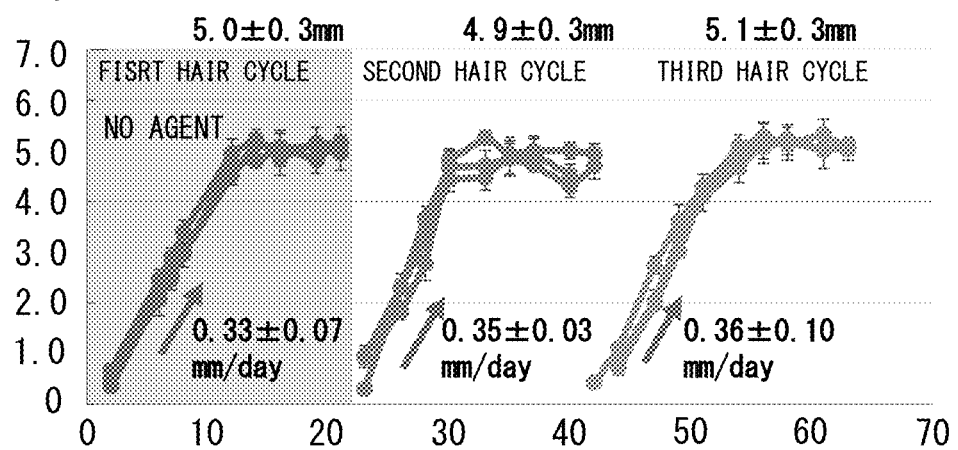
FIG. 13 is a chart showing changes in hair shaft length in sites of mice where a 50% ethanol aqueous solution containing muco-inositol (5 wt %) was applied. The vertical axis represents hair shaft length (mm) and the horizontal axis represents the number of days. Here, the first hair cycle shows reference data in which a 50% ethanol aqueous solution not containing the agent was applied.
Figure 14:
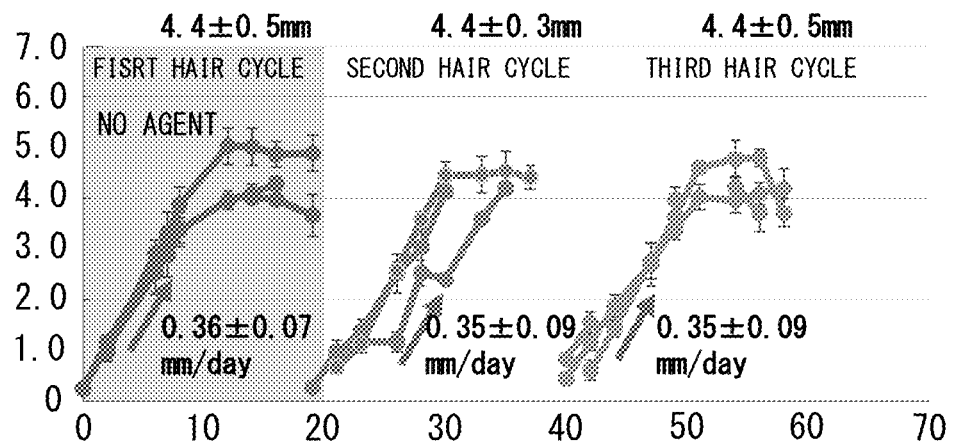
FIG. 14 is a chart showing changes in hair shaft length in sites of mice where a 50% ethanol aqueous solution containing scyllo-inositol (5 wt %) was applied. The vertical axis represents hair shaft length (mm) and the horizontal axis represents the number of days. Here, the first hair cycle shows reference data in which a 50% ethanol aqueous solution not containing the agent was applied.

As is clear from Tables 1 to 3 and FIGS. 1 to 3, when D-chiro-inositol was contained 10 wt %, 5 wt %, or 1 wt % as the agent, both the hair shaft growth rate and hair shaft maximum length were increased significantly relative to the reference data, indicating hair growth activity. Meanwhile, as is clear from Table 4 and FIG. 4, when D-chiro-inositol was contained 0.1 wt % as the agent, the hair shaft growth rate was not significantly different from the reference data while the hair shaft maximum length was increased significantly in the third hair cycle. Hence, in view of a positive effect on at least hair shaft length, hair growth activity was shown in the case in which D-chiro-inositol was contained 0.1 wt %. Further, as is clear from Table 5 and FIG. 5, when D-chiro-inositol was contained 0.01 wt %, both the hair shaft growth rate and hair shaft maximum length showed marginally significant differences from the reference data in this experiment. Accordingly, it is suggested that the effective lower limit of hair growth activity of D-chiro-inositol is from 0.001 wt % to 0.01 wt % in terms of D-chiro-inositol content.

As for stereoisomers of chiro-inositol, as is clear from Tables 6 to 14 and FIGS. 6 to 14, significant differences relative to the reference data were not observed in both the hair shaft growth rate and hair shaft maximum length in this experiment, and hence, hair growth activity was not confirmed in all the cases in which 5 wt % of L-chiro-inositol, 5 wt % or 1 wt % of myo-inositol, 5 wt % or 1 wt % of allo-inositol, 5 wt % or 1 wt % of epi-inositol, 5 wt % of muco-inositol, or 5 wt % of scyllo-inositol was contained.

Example 2 Evaluation of D-chiro-Inositol Hair Growth Activity (2)

From a viewpoint of an increase in hair shaft diameter (thickness), the hair growth activity of D-chiro-inositol was evaluated.

In C57BL6/N mice, it is known that when body hair of the back is pulled out, hair cycles in the pulled-out region are forced to shift to the catagen phase, and as a result, the hair cycles in the pulled-out region are synchronized. Therefore, only hair in the anagen phase becomes observable by decreasing variations in hair cycles. Approximately 7 days after hair is pulled out, as a sign of the anagen phase, skin color changing into gray is observed as melanocytes in hair follicles start synthesizing melanin, in addition to growth of pigmented hair. Further, approximately 10 days after hair is pulled out, new hair growth is observed in the pulled-out region. Approximately 21 days after hair is pulled out, the boundary between the pulled-out region and non-pulled-out region becomes invisible and the hair cycles enter the catagen phase, and hair shaft growth is arrested. Accordingly, hair growth activity can be evaluated from a viewpoint of an increase in hair shaft diameter by measuring the hair shaft diameter of body hair grown in the pulled-out region approximately 21 days after hair is pulled out.

In this Example, the body hair of the back of C57BL/6N mice (7 weeks of age, female) was pulled out, and a test solution in which D-chiro-inositol (from Wako Pure Chemical Industries Ltd.) was dissolved in 50% ethanol at a concentration of 1 wt % was applied to the pulled-out region over 21 days (once/day, 100 µl).

The application was performed for two groups (test solution-applied group and negative control group (50% ethanol-applied group)), where each group consisted of six mice. Hair shafts in the applied regions were collected with tweezers on day 21 after the application. About 20 hair shafts were collected from each mouse, and the hair shaft diameter was measured for 10 hair shafts randomly selected from 120 hair shafts in total collected from 6 mice of each group. The hair shaft diameter was calculated by measuring diameters at three different sites of each hair shaft within one field of view under an optical microscope, regarding the average value of these diameters as the diameter of each hair shaft, and averaging the diameters of 10 hair shafts derived by the same measurement. The results are shown in FIG. 15.

Figure 15:
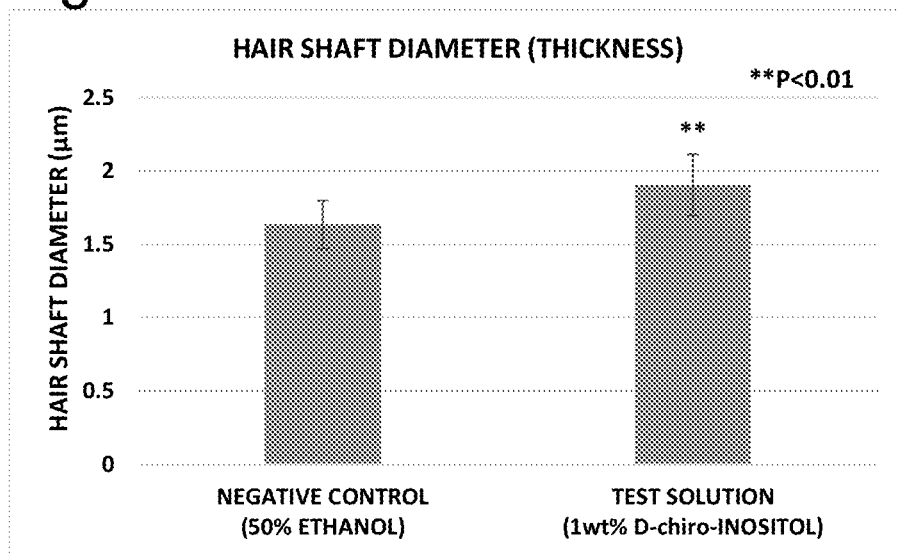
FIG. 15 is a graph showing the hair shaft diameter of body hair grown on day 21 in hair-removed portions of test solution-applied C57BL/6N mice, to which a 50% ethanol aqueous solution containing D-chiro-inositol (1 wt %) was applied, and of negative control C57BL/6N mice, to which a 50% ethanol aqueous solution was applied. The vertical axis represents hair shaft diameter. The mark ** indicates significance with $P<0.01$.

As is clear from FIG. 15, the test solution-applied group and the negative control group exhibited a remarkable difference in hair shaft diameter on day 21 after the application, and the hair shaft diameter of the test solution-applied group was significantly larger. Accordingly, the hair growth activity of D-chiro-inositol was confirmed also from a viewpoint of an increase in hair shaft diameter.

Example 3 Evaluation of New Hair Growth Promoting Activity of D-chiro-Inositol

The hair follicle that produces a hair shaft is the only organ known to repeat growth and regression over the entire life. Such regular growth and regression are divided into the anagen phase, the catagen phase, and the telogen phase of a hair cycle. The body hair of the back of C3H/He mice is bound to be in the telogen phase 45 to 95 days after birth, and thus an extremely long telogen phase-bound period is observed compared with common mice, such as C57BL/6N mice, whose hair cycle of the body hair of the back lasts about 21 days in total for the anagen phase, the catagen phase, and the telogen phase. Typically, when the hair follicle enters the anagen phase, the skin increasingly exhibits its gray color, and new hair growth is confirmed by observing regenerated hair gradually appearing on the skin. Therefore, by using C3H/He mice at 45 to 90 days after birth, new hair growth promoting activity can be evaluated.

In this Example, the hair of the back of C3H/He mice (Japan SLC, Inc.) (8 weeks of age, female), whose hair cycles were in the telogen phase, was shortened with hair clippers, followed by complete removal of the body hair (dehairing) of the back by using a depilatory. After 24 hours of a recovery period, a test solution in which D-chiro-inositol (from Wako Pure Chemical Industries Ltd.) was dissolved in a 50% ethanol at a concentration of 5 wt % was applied to the hair-removed region (once/day, 100 µl) over 21 days.

Figure 16:
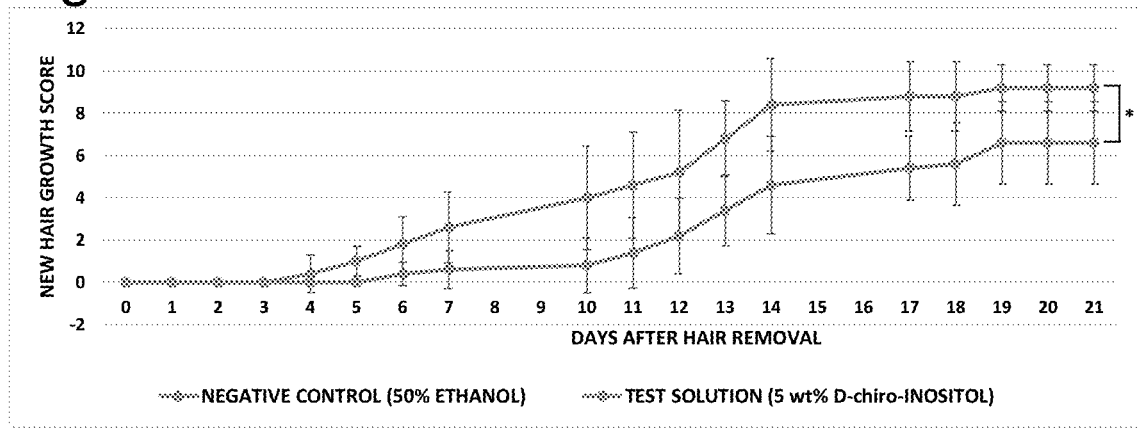
FIG. 16 is a chart showing changes in new hair growth score over time for test solution-applied C3H/He mice, to which a 50% ethanol aqueous solution containing D-chiro-inositol (1 wt %) was applied, and for negative control C3H/He mice, to which a 50% ethanol aqueous solution was applied. The vertical axis represents total new hair growth score and the horizontal axis represents the number of days after hair removal. The mark * indicates significance with $P<0.05$.
Figure 17:
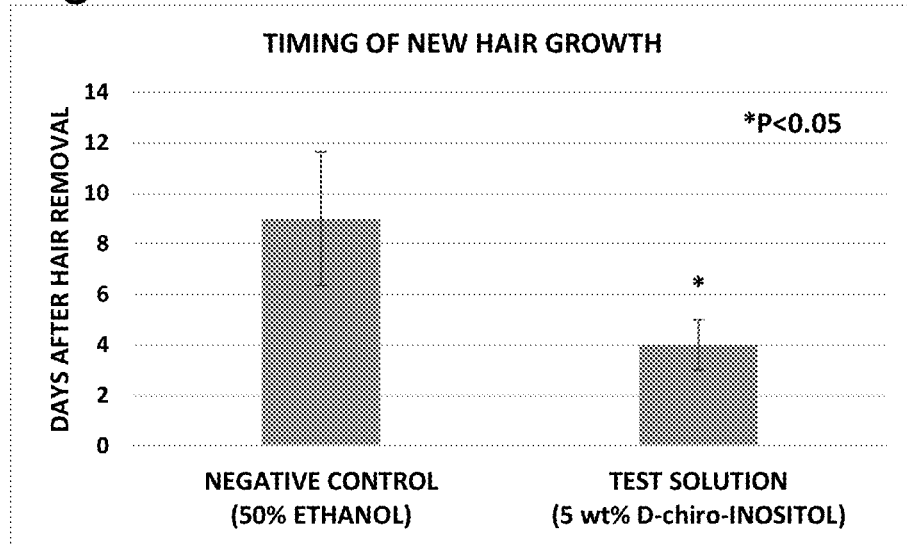
FIG. 17 is a graph showing the timing of new hair growth for test solution-applied C3H/He mice, to which a 50% ethanol aqueous solution containing D-chiro-inositol (1 wt %) was applied, and for negative control C3H/He mice, to which a 50% ethanol aqueous solution was applied. The vertical axis represents the number of days to reach a new hair growth score of 1 or more after hair removal. The mark * indicates significance with $P<0.05$.

The application was performed for two groups (test solution-applied group and negative control group (50% ethanol-applied group)), where each group consisted of five mice. On the basis of new hair growth score criteria (Table 15) according to appearance changes in a portion of the applied region that leaves the telogen phase and enters a regeneration phase, the degree of new hair growth in the applied region was quantified (range of 1 to 10 in which new hair growth scores concerning two items are summed) over time on day 0, 4, 5, 6, 7, 10, 11, 12, 13, 14, 17, 18, 19, 20, and 21 after hair removal. A higher numerical value indicates a higher degree of new hair growth. Each numerical value was calculated as an average score of 5 mice in each group. Further, the same test was performed three times and the timing of new hair growth after hair removal was calculated as the number of days. The new hair growth promoting activity was thus investigated also from a viewpoint of the telogen phase in a hair cycle shortened by D-chiro-inositol, relative to the negative control. The results are shown in FIGS. 16 and 17.

[Table 15]

TABLE 15

New Hair Growth Score Criteria according to Appearance Changes

| Area ratio of portion that has entered new hair growth phase | | Appearance of portion that has entered new hair growth phase | |
|---|---|---|---|
| — | 0 | — | 0 |
| Fractional | 1 | Light gray | 1 |
| Up to ⅓ | 2 | Dark gray | 2 |
| ⅓ to ⅔ | 3 | Up to ⅓ is newly grown hair shaft | 3 |
| Almost all | 4 | Up to ⅔ is newly grown hair shaft | 4 |
| All | 5 | All is newly grown hair shaft | 5 |

As is clear from FIG. 16, a remarkable difference in new hair growth score was observed on day 21 after hair removal between the test solution-applied group and the negative control group, and the new hair growth score of the test solution-applied group was significantly higher. Hence, the new hair growth promoting activity of D-chiro-inositol was confirmed.

Further, FIG. 17 shows, as the number of days after hair removal, the timing of new hair growth, at which the new hair growth score of each group reached 1 or more. An average timing of new hair growth for the negative control group was on day 9, whereas that for the test solution-applied group was on day 4. Hence, shortening of the telogen phase in a hair cycle by D-chiro-inositol was confirmed.

Example 4 New Hair Growth Test in Monkey

As an animal model of humans, a new hair growth test was performed by using a monkey.

A crab-eating macaque (*Macaca fascicularis*) is a monkey (class: Mammalia, order: Primates, family: Cercopithecidae, genus: *Macaca*) that has many similarities to humans, such as the morphology of the temporomandibular joint, and is frequently employed as a laboratory animal for morphological studies and medication studies due to its easy breeding and rearing. The crab-eating macaque is known for the replacement of the body hair in a six-month cycle in a year. Among aged female monkeys that had babies repeatedly and aged male monkeys of low social status, individuals with observed symptoms of hair thinning or sparse hair emerge with low frequency. The portions of hair thinning or sparse hair of these individuals are in a state in which hair shafts do not protrude from pores or cannot be observed with the naked eye due to marked shortening or thinning.

In this Example, to an aged crab-eating macaque (19 years of age, male) having sparse body hair of the head, a test solution A in which D-chiro-inositol (from Wako Pure Chemical Industries Ltd.) was dissolved in 50% ethanol at a concentration of 1 wt % and a test solution B in which myo-inositol was dissolved in 50% ethanol at a concentration of 1 wt % were applied every day to about 4 $cm^2$-sparse hair regions (2 cm×2 cm) in both left and right sides across the median line of the head of the macaque. The application (once/day, 150 µl) was performed over 8 weeks, and 50% ethanol was applied as a negative control. At the end of 8 weeks, hair shafts in the applied regions were cut with hair clippers while leaving 2 to 3 mm from pores toward the outside of the body, and the total number of hair protruded from the pores in the applied regions was counted. A new hair growth rate was calculated as an increase rate in the number of hair at the end of 8 weeks, relative to the number of hair protruded from pores in the same regions before the application at the start of the test as 100%. The results are shown in Table 16.

TABLE 16

Results of New Hair Growth Test in Monkey

| | Negative control (50% ethanol) | Test solution A (1 wt % D-chiro-inositol) | Test solution B (1 wt % myo-inositol) |
|---|---|---|---|
| New hair growth rate (%) | 109.5 | 175.9 | 107.1 |

As is clear from Table 16, a remarkably higher new hair growth rate than the cases of the test solution B and the negative control was obtained by application of the test solution A. Hence, the new hair growth promoting activity of D-chiro-inositol was also confirmed in a monkey. Although the data is not shown, hair shafts in the test solution A-applied region became remarkably thicker than those in the cases of the test solution B and the negative control. Hence, the hair shaft growth promoting activity of D-chiro-inositol was also confirmed in a monkey.

Example 5 Hair Papilla Cell Proliferation Test by Two-dimensional Culture

Hair papilla cells transmit new hair growth signals to hair matrix cells via signaling substances to activate hair matrix cells, thereby controlling processes of new hair growth and hair elongation. Accordingly, the hair shaft growth promoting activity and the like of test substances can be evaluated from a proliferation rate of hair papilla cells.

In this Example, the skin of the whisker region was taken from a C57BL/6N mouse and hair papillae were harvested from isolated whisker follicles under a stereo microscope. Six hair papillae were fixed to the bottom surface of a 60 mm-plastic petri dish (from Sumitomo Bakelite Co., Ltd.), and the primary culture was performed at 37° C. in the presence of 5% $CO_2$ by using a hair papilla cell culture medium in which 2% FCS (fetal calf serum), 0.6% ITT (insulin-transferrin-triiodothyronine mixture), 1% BPE (bovine pituitary extract), and 0.6% Cyp (cyproterone solution) were added to a PCGM base medium. Afterwards, the medium was replaced every 2 to 3 days and subculturing was repeated about every two weeks. In this experiment, hair papilla cells at passage 3 or less were used. First, the hair papilla cells were seeded in a 24-well microplate for cell culture (from Sumitomo Bakelite Co., Ltd.) at 10,000 cells/well and cultured for 3 days by using a test solution A that was a hair papilla cell culture medium to which D-chiro-inositol dissolved in PBS was added at a final concentration of 0.1 wt %, a test solution B that was a hair papilla cell culture medium to which myo-inositol dissolved in PBS was added at a final concentration of 0.1 wt %, and a negative control that was a hair papilla cell culture medium to which PBS alone was added. The number of cells after culturing for 3 days was counted by using a hemocytometer, and proliferation rates in test solution A and the test solution B were calculated relative to 100% for a proliferation rate in the negative control as 100%. The results are shown in FIG. 18.

Figure 18:
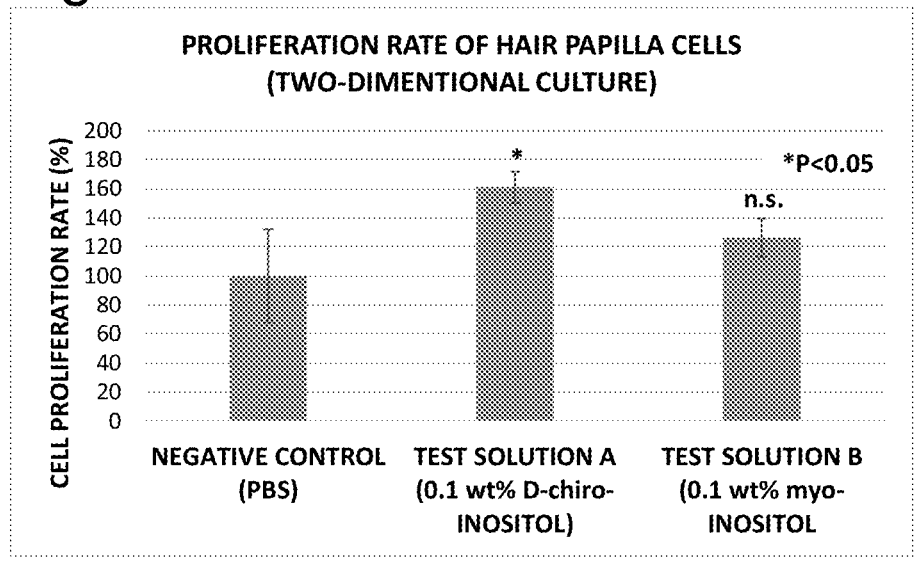
FIG. 18 is a graph showing the results of hair papilla cell proliferation tests performed by a two-dimensional culture method using, as media, a test solution A in which D-chiro-inositol was added to a hair papilla cell culture medium (final concentration of 0.1 wt %), a test solution B in which myo-inositol was added to a hair papilla cell culture medium (final concentration of 0.1 wt %), and a negative control in which PBS alone was added to a hair papilla cell culture medium. The vertical axis represents a cell proliferation rate (%) relative to the negative control. The mark * indicates significance with $P<0.05$.

As is clear from FIG. 18, in the case of culturing by using the test solution A, a proliferation rate was increased significantly compared with the case of culturing by using the negative control. Hence, the hair papilla cell proliferation promoting activity of D-chiro-inositol was confirmed. Meanwhile, in the case of culturing by using the test solution B, no significant difference was observed, and hence, the hair papilla cell proliferation promoting activity of myo-inositol was not confirmed.

Example 6 Hair Papilla Cell Proliferation Test by Three-dimensional Culture

In a three-dimensional culture method, cell proliferation is calculated from the area of three-dimensional cell spheroids which simulate conditions further close to in vivo ones, and hence, cell proliferation can be evaluated in terms of integrated two factors of cell growth and an increase in cell count.

In this Example, hair papilla cells prepared in a similar manner to Example 5 were seeded in a 96-well U-bottom microplate for cell culture (from Sumitomo Bakelite Co., Ltd.) at 6,000 cells/well and centrifuged with a plate centrifuge at room temperature and at a rotating speed of 1,000 rpm for 1 minute to yield three-dimensional hair papilla cell spheroids. The spheroids were cultured for 3 days by using each of test solutions A1 to A3 that were hair papilla cell culture media to which D-chiro-inositol dissolved in PBS was added at a final concentration of 0.05 wt %, 0.1 wt %, or 1 wt %; test solutions B1 to B3 that were hair papilla cell culture media to which myo-inositol dissolved in PBS was added at a final concentration of 0.05 wt %, 0.1 wt %, or 1 wt %; and a negative control that was a hair papilla cell culture medium to which PBS alone was added. The spheroids after culturing for 3 days were imaged by using a VHX2000 digital microscope (Keyence Corporation), and the area of the spheroids was calculated by using a digital microscope analysis tool. By calculating a spheroid area increase rate in the test solutions A1 to A3 and B1 to B3, relative to an area increase rate in the negative control as 100%, the proliferation of hair papilla cells in conditions further close to in vivo condition was quantified. The results are shown in FIG. 19.

Figure 19:
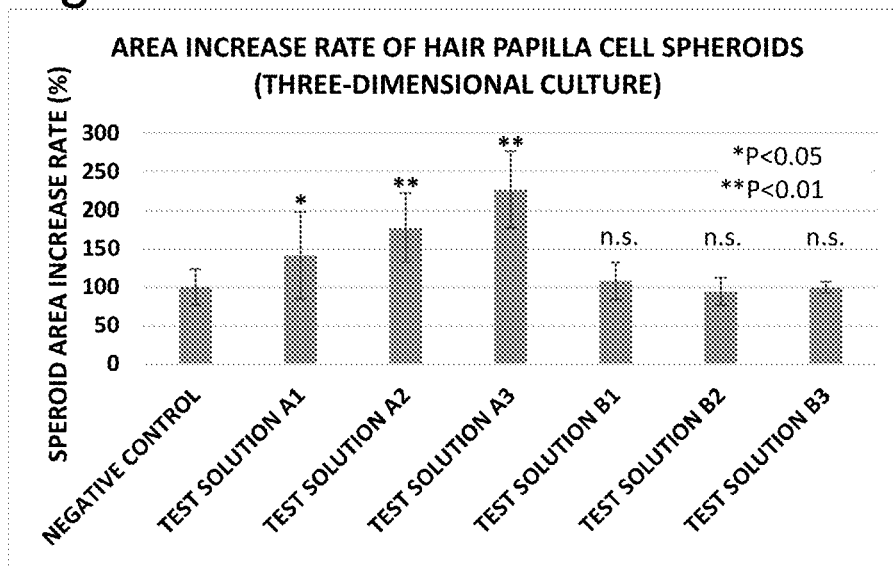
FIG. 19 is a graph showing the results of hair papilla cell proliferation tests performed by a three-dimensional culture method using, as media, test solutions A1 to A3 in which D-chiro-inositol was added to hair papilla cell culture media (final concentrations of 0.05, 0.1, and 1 wt %), test solutions B1 to B3 in which myo-inositol was added to hair papilla cell culture media (final concentrations of 0.05, 0.1, and 1 wt %), and a negative control in which PBS alone was added to a hair papilla cell culture medium. The vertical axis represents an area increase rate (%) of hair papilla cell spheroids, relative to the negative control. The mark * indicates significance with $P<0.05$, and the mark ** indicates significance with $P<0.01$.

As is clear from FIG. 19, in the cases of culturing by using the test solutions A1 to A3, the spheroid area was increased significantly compared with the case of culturing by using the negative control. Hence, the hair papilla cell proliferating activity of D-chiro-inositol was confirmed at all the tested final concentrations of 0.05 wt %, 0.1 wt %, and 1 wt %. Meanwhile, no significant differences were observed in the cases of culturing by using the test solutions B1 to B3, and hence, the hair papilla cell proliferation promoting activity of myo-inositol was not confirmed at any of the tested final concentrations of 0.05 wt %, 0.1 wt %, and 1 wt %. Here, from the degree of the spheroid area increase rates, an increase in cell count is considered to largely contribute to the proliferation of hair papilla cells in the cases of culturing by using the test solutions A1 to A3.

The invention claimed is:

1. A method of growing hair comprising administering a hair growth agent comprising an effective amount of D-chiro-inositol externally to a subject, wherein D-chiro-inositol content is 1 to 10 wt % based on a total weight and wherein the hair growth agent is used for promoting hair shaft growth or for growing new hair.

2. The method according to claim 1, wherein the hair growth agent is used for increasing an elongation rate of a hair shaft.

3. The method according to claim 1, wherein the hair growth agent is used for increasing a maximum length of a hair shaft.

4. The method according to claim 1, wherein the hair growth agent is used for increasing a hair shaft diameter.

5. The method according to claim 1, wherein the hair growth agent is used for increasing a hair count.

6. The method according to claim 1, wherein the hair growth agent is used for promoting new hair growth from a pore where new hair growth has been arrested or ability of the pores to grow new hair has decreased.

7. The method according to claim 1, wherein the hair growth agent is used for shortening the telogen phase in a hair cycle.

8. The method according to claim 1, wherein the hair growth agent is used for resuming an arrested hair cycle.

9. The method according to claim 1, wherein the hair growth agent is a solution.

10. The method according to claim 1, wherein the hair growth agent is used for human scalp hair.

* * * * *